United States Patent
Tanaka et al.

(10) Patent No.: US 9,973,714 B2
(45) Date of Patent: May 15, 2018

(54) IMAGING DEVICE AND METHOD

(71) Applicant: FUJIFILM Corporation, Tokyo (JP)

(72) Inventors: Yasutake Tanaka, Ashigarakami-gun (JP); Yasunori Ohta, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 64 days.

(21) Appl. No.: 15/047,170

(22) Filed: Feb. 18, 2016

(65) Prior Publication Data

US 2016/0269660 A1    Sep. 15, 2016

(30) Foreign Application Priority Data

Mar. 12, 2015    (JP) .................................. 2015-049060

(51) Int. Cl.
*H04N 5/235*    (2006.01)
*H04N 5/238*    (2006.01)
(Continued)

(52) U.S. Cl.
CPC ......... *H04N 5/35581* (2013.01); *G01N 21/55* (2013.01); *G01N 21/59* (2013.01);
(Continued)

(58) Field of Classification Search
CPC ...... H04N 5/355–5/3559; H04N 5/235–5/243; H04N 5/353–5/3537;
(Continued)

(56) References Cited

U.S. PATENT DOCUMENTS 7,852,402 B2 * 12/2010 McGarvey ........... H04N 3/1568
                                                                 348/243
2011/0032499 A1 * 2/2011 Kawashima ........... G03B 27/42
                                                                 355/53
(Continued)

FOREIGN PATENT DOCUMENTS

JP          2001-24950 A      1/2001
JP          2004-128546 A     4/2004
(Continued)

OTHER PUBLICATIONS

Extended European Search Report, dated Aug. 16, 2016, for European Application No. 16155107.2.
(Continued)

*Primary Examiner* — Xi Wang
(74) *Attorney, Agent, or Firm* — Birch, Stewart, Kolasch & Birch, LLP

(57) ABSTRACT

Disclosed is an imaging device and method capable of obtaining an image with exposure appropriate for each sample when a plurality of samples are collectively imaged. For performing imaging using an imaging device configured to divide an imaging area into a plurality of partial areas, to perform imaging for each partial area, a proper exposure time is calculated for each partial area based on an image signal, a positive integer multiple of the maximum value among the calculated proper exposure times is set as a total imaging time, an imaging frequency is set for each partial area using a value obtained by dividing the total imaging time by the calculated proper exposure time, imaging with the calculated proper exposure time of the partial area is successively and repeatedly performed by the set imaging frequency, and each image successively imaged is simply added or is added and averaged.

20 Claims, 7 Drawing Sheets

(51) Int. Cl.
*H04N 5/355* (2011.01)
*G01N 21/55* (2014.01)
*G01N 21/59* (2006.01)
*G01N 21/64* (2006.01)
*G01N 21/76* (2006.01)
*H04N 5/347* (2011.01)

(52) U.S. Cl.
CPC ......... *G01N 21/6456* (2013.01); *G01N 21/76* (2013.01); *H04N 5/2351* (2013.01); *H04N 5/347* (2013.01)

(58) Field of Classification Search
CPC .......... G06T 5/007–5/009; G06T 2207/20208; G03B 7/00–7/28; G03B 2207/00–2207/005; G03B 9/58–9/62
USPC ............................ 348/362–368; 396/213–262
See application file for complete search history.

(56) References Cited

U.S. PATENT DOCUMENTS

| | | | |
|---|---|---|---|
| 2012/0002082 A1* | 1/2012 | Johnson | G06T 5/50 348/234 |
| 2013/0070110 A1 | 3/2013 | Yamaguchi | |
| 2014/0028873 A1* | 1/2014 | Higuchi | G06K 9/2054 348/229.1 |
| 2015/0015760 A1 | 1/2015 | Tsunai | |
| 2015/0109479 A1* | 4/2015 | Kimoto | H04N 5/23212 348/231.99 |
| 2016/0112644 A1 | 4/2016 | Nishi | |

FOREIGN PATENT DOCUMENTS

| | | |
|---|---|---|
| JP | 2007-184814 A | 7/2007 |
| JP | 2013-68725 A | 4/2013 |
| WO | WO 2013/145765 A1 | 10/2013 |
| WO | WO 2014/192152 A1 | 12/2014 |

OTHER PUBLICATIONS

Japanese Office Action dated Feb. 6, 2018 for corresponding Japanese Patent Application No. 2015-049060 (with English Translation).

* cited by examiner

IMAGING DEVICE AND METHOD

CROSS-REFERENCE TO RELATED APPLICATIONS

The present application claims priority under 35 U.S.C. § 119 to Japanese Patent Application No. 2015-049060, filed on Mar. 12, 2015. Each of the above application(s) is hereby expressly incorporated by reference, in its entirety, into the present application.

BACKGROUND OF THE INVENTION

1. Field of the Invention

The present invention relates to an imaging device and method which images light emitted from an object with an imaging element.

2. Description of the Related Art

Hitherto, an imaging system which arranges an object in a housing and images chemiluminescence, fluorescence, or reflected light from the object, or transmitted light transmitted through the object using a light source in the housing has been used. For example, JP2004-128546A discloses an imaging system which arranges a plurality of samples at intervals on the surface of a carrier, such as a glass slide plate or a membrane filter, and collectively images chemiluminescence or fluorescence emitted from a plurality of samples through single imaging.

JP2004-128546A suggests that, since chemiluminescence or fluorescence emitted from each sample is weak, and it is not easy to accurately calculate an exposure time optimum for imaging in advance, a shutter is released at each predetermined comparatively short exposure time to perform photoelectric conversion, and an image signal at each predetermined exposure time subjected to photoelectric conversion is sequentially added to generate a plurality of images with different exposure times, a plurality of images are displayed in parallel on a display screen, and an image with an exposure time appropriate for analysis is selectable from among a plurality of images.

SUMMARY OF THE INVENTION

On the other hand, a plurality of samples for use in imaging may vary in light emission intensity, and in this case, there is a problem in that, in imaging at a single exposure time, exposure is excessively strong or excessively weak in some samples and it is not possible to obtain an image with exposure appropriate for each sample. JP2004-128546A suggests that an exposure time applied to a plurality of samples uniformly is selectable, but there is no description of a method which obtains an image with exposure appropriate for each sample.

An object of the invention is to provide an imaging device and method capable of an image with exposure appropriate for each sample even if a plurality of samples are collectively imaged, in consideration of the above-described situation.

An imaging device of the invention includes an imaging unit which is configured to divide an imaging area imaging an object into a plurality of partial imaging areas, to perform imaging for each partial imaging area, and to output the captured image, a proper exposure time calculation unit which calculates a proper exposure time for each partial imaging area based on an image signal acquired in the partial imaging area, an imaging frequency setting unit which sets a total imaging time as a positive integer multiple of the maximum value among the plurality of calculated proper exposure times, and sets an imaging frequency for each partial imaging area using a value obtained by dividing the total imaging time by the calculated proper exposure time of the partial imaging area, an imaging control unit which performs control such that, in each partial imaging area, the imaging unit successively and repeatedly performs imaging with the calculated proper exposure time of the partial imaging area by the set imaging frequency of the partial imaging area, and an image processing unit which simply adds or adds and averages each image successively imaged in each partial imaging area.

In the imaging device of the invention, the imaging area may be constituted of an imaging element from which an image signal is readable nondestructively.

The imaging device of the invention may further include an input unit which receives an input from the user, and when an input for designating how the imaging area is divided is received by the input unit, the imaging unit may divide the imaging area into a plurality of partial imaging areas according to the designation.

In the imaging device of the invention, the imaging unit may perform pre-imaging in the imaging area, and the proper exposure time calculation unit may calculate the proper exposure time based on an image signal of each partial imaging area acquired through the pre-imaging performed in the imaging area.

In the imaging device of the invention, when the total imaging time is Ttotal, a natural number equal to or less than the number of partial imaging areas is i, a proper exposure time of an i-th partial imaging area among the plurality of partial imaging areas is $T(i)$, an integer part of a value obtained by dividing the total imaging time by the proper exposure time of the i-th partial imaging area is $N(i)$, and a threshold value determined in advance is Tth1, for the partial imaging area where $Ttotal-(T(i) \times N(i)) \geq Tth1$, the imaging frequency setting unit may set a value obtained by adding 1 to $N(i)$ as the imaging frequency of the partial imaging area.

In the imaging device of the invention, the imaging control unit may perform control such that the imaging unit successively and repeatedly performs imaging with the proper exposure time of the partial imaging area to the $N(i)$-th time and then performs the $(N(i)+1)$th imaging with an exposure time of $Ttotal-(T(i) \times N(i))$ exceptionally in the partial imaging area where $Ttotal-(T(i) \times N(i)) \geq Tth1$.

In the imaging device of the invention, the imaging frequency setting unit may set $N(i)$ as the imaging frequency of the partial imaging area for the partial imaging area where $0 < Ttotal-(T(i) \times N(i)) < Tth1$, and the image processing unit may multiply each pixel value of an image obtained by simply adding or adding and averaging each image successively imaged in the partial imaging area by a value of $Ttotal/(T(i) \times N(i))$ for the partial imaging area where $0 < Ttotal-(T(i) \times N(i)) < Tth1$.

In the imaging device of the invention, when the total imaging time is Ttotal, a natural number equal to or less than the number of partial imaging areas is i, a proper exposure time of an i-th partial imaging area among the plurality of partial imaging areas is $T(i)$, an integer part of a value obtained by dividing the total imaging time by the proper exposure time of the i-th partial imaging area is $N(i)$, and a threshold value determined in advance is Tth2, the imaging frequency setting unit may set a value obtained by adding 1 to $N(i)$ as the imaging frequency of the partial imaging area for the partial imaging area where $(T(i) \times (N(i)+1))-Ttotal \leq Tth2$.

In the imaging device of the invention, the image processing unit may multiply each pixel value of an image obtained by simply adding or adding and averaging each image successively imaged in the partial imaging area by a value of Ttotal/(T(i)×(N(i)+1)) for the partial imaging area where (T(i)×(N(i)+1))−Ttotal≤Tth2.

An imaging method of the invention which performs imaging using the imaging device having an imaging unit configured to divide an imaging area imaging an object into a plurality of partial imaging areas, to perform imaging for each partial imaging area, and to output the captured image includes calculating a proper exposure time for each partial imaging area based on an image signal acquired in the partial imaging area, setting a total imaging time as a positive integer multiple of the maximum value among the plurality of calculated proper exposure times, and setting an imaging frequency for each partial imaging area using a value obtained by dividing the total imaging time by the calculated proper exposure time of the partial imaging area, successively and repeatedly performing imaging with the calculated proper exposure time of the partial imaging area in each partial imaging area by the set imaging frequency of the partial imaging area, and simply adding or adding and averaging each image successively imaged in each partial imaging area.

According to the imaging device and method of the invention, for performing imaging using an imaging device having an imaging unit configured to divide an imaging area imaging an object into a plurality of partial imaging areas, to perform imaging for each partial imaging area, and to output the captured image, a proper exposure time is calculated for each partial imaging area based on an image signal acquired in the partial imaging area, a positive integer multiple of the maximum value among a plurality of calculated proper exposure times is set as a total imaging time, an imaging frequency is set for each partial imaging area using a value obtained by dividing the total imaging time by the calculated proper exposure time of the partial imaging area, imaging with the calculated proper exposure time of the partial imaging area is successively and repeatedly performed by the set imaging frequency of the partial imaging area in each partial imaging area, and each image successively imaged in each partial imaging area is simply added or is added and averaged. With this, for example, when a plurality of samples are collectively imaged, imaging is performed while assigning a plurality of samples to a plurality of partial imaging areas, and in each partial imaging area, it is possible to perform imaging with an exposure time suitable for a sample imaged in each partial imaging area, and to obtain an image with exposure suitable for each sample.

As described above, in the imaging device and method of the invention, since imaging with the proper exposure time is successively and repeatedly performed by the set imaging frequency in each partial imaging area, and each image successively imaged is simply added or added and averaged, it is possible to improve the signal-noise ratio (S/N) of the image imaged in each partial imaging area. In the case of simple addition, since a signal component becomes n times, and a noise component becomes √n times, the S/N is improved to √n times. In the case of addition averaging, since a signal component becomes one time, and a noise component becomes 1/√n times, the S/N is improved to √n times.

DESCRIPTION OF THE PREFERRED EMBODIMENTS

Figure 1:
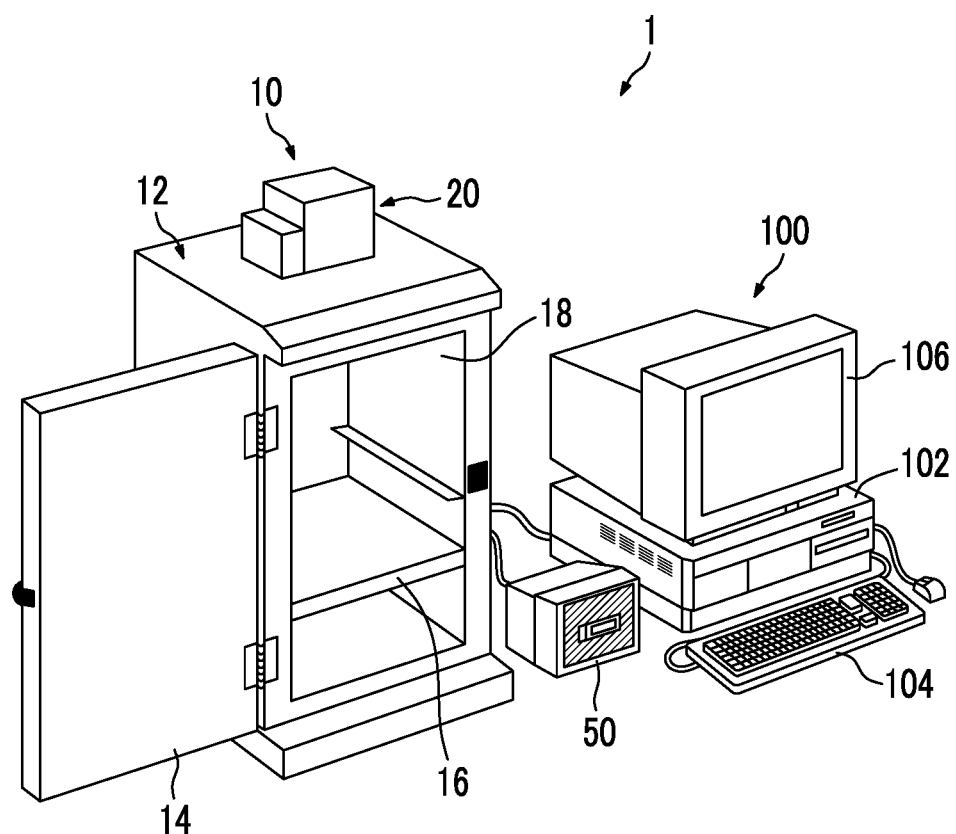
FIG. 1 is a schematic perspective view of an imaging system including an embodiment of the invention.

Hereinafter, an imaging system 1 including an embodiment of an imaging device and method of the invention will be described referring to the drawings. FIG. 1 is a schematic perspective view showing the imaging system 1, FIG. 2 is a schematic sectional view showing the internal configuration of a black box constituting a part of the imaging system 1, and FIG. 3 is a schematic block diagram showing an imaging system.

Figure 2:
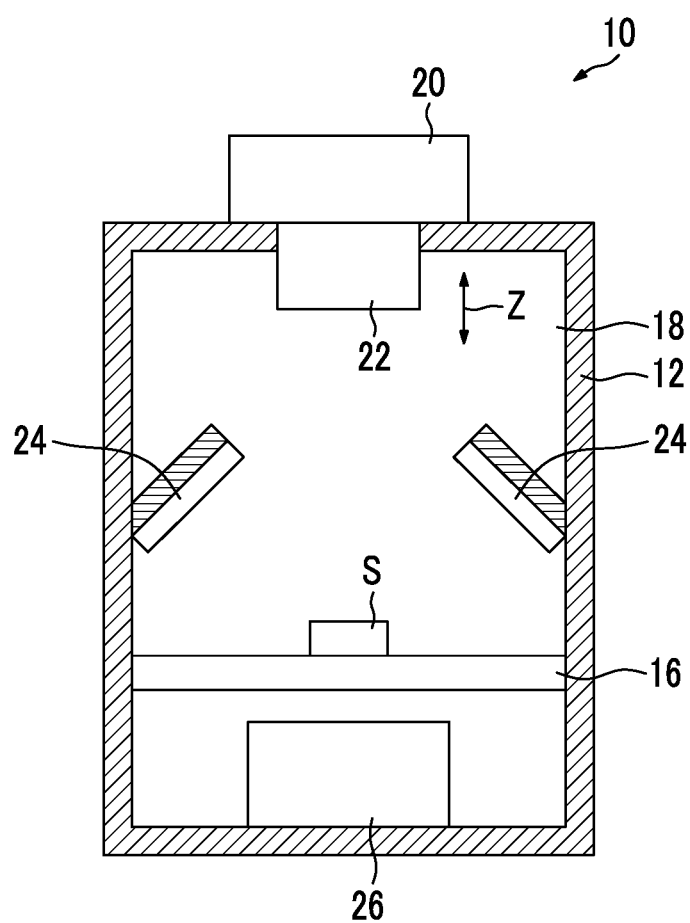
FIG. 2 is a schematic sectional view showing the internal configuration of a black box.
Figure 3:
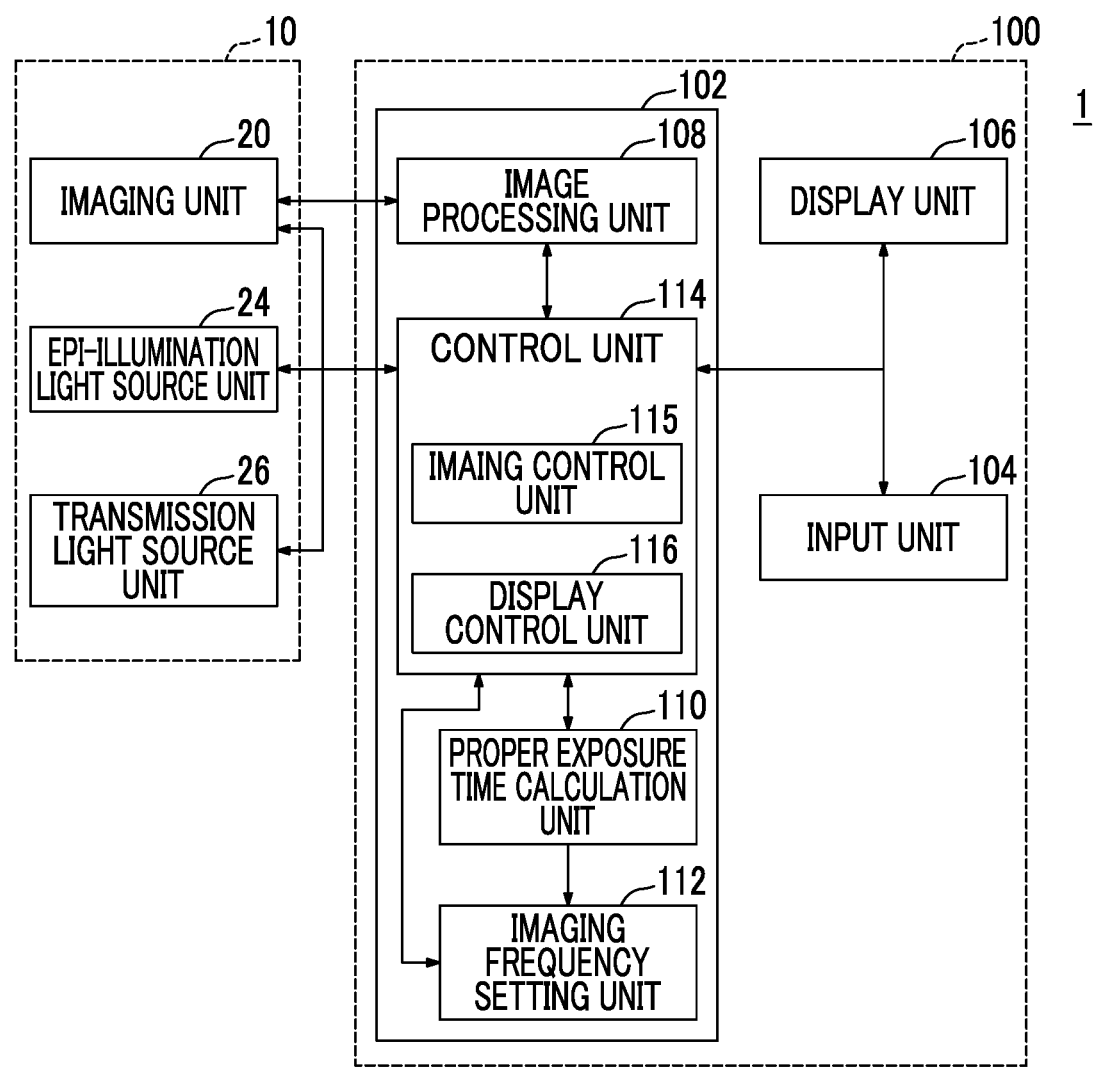
FIG. 3 is a schematic block diagram of the imaging system of FIG. 1.

As shown in FIGS. 1 and 2, the imaging system 1 of this embodiment includes a black box 10 and an imaging control device 100. The black box 10 includes a housing 12 having a door 14, a stage 16 on which an object S is arranged, an imaging unit 20, a lens unit 22, an epi-illumination light source unit 24, a transmission light source unit 26, and an object observation monitor 50.

The housing 12 has a hollow portion 18 which is formed in a substantially rectangular parallelepiped, and is provided with the stage 16 on which the object S is arranged. The door 14 shown in FIG. 1 is openably attached to the housing 12, and the user opens the door 14, arranges the object S on the stage 16, and closes the door 14, thereby accommodating the object S in the housing 12. The housing 12 constitutes a black box such that external light does not enter the hollow portion 18. The stage 16 is formed of a material which transmits light from the transmission light source unit 26.

The imaging unit 20 includes an imaging area which images the object to generate an image signal, and a reading unit which reads the image signal from the imaging area, and is configured to divide the imaging area into a plurality of partial imaging areas R(i) (where i is a natural number equal to or less than the number of partial imaging areas) and to perform reading of the image signal in units of the partial imaging areas or reset of the stored electric charge. For example, an imaging area is constituted of a complementary metal-oxide semiconductor (CMOS) image sensor which can perform reading of an image signal in units of pixels or reset of the stored electric charge, or a thin film transistor (TFT) image sensor, and reading of the image signal of each partial imaging area or reset of the stored electric charge can be performed. For example, a plurality of charge coupled device (CCD) image sensor modules of a size corresponding to the partial imaging area may be arranged in a two-dimensional manner to constitute the entire imaging area, and reading of an image signal of each CCD image sensor module (that is, each partial imaging area) or reset of the stored electric charge can be performed.

Figure 4:
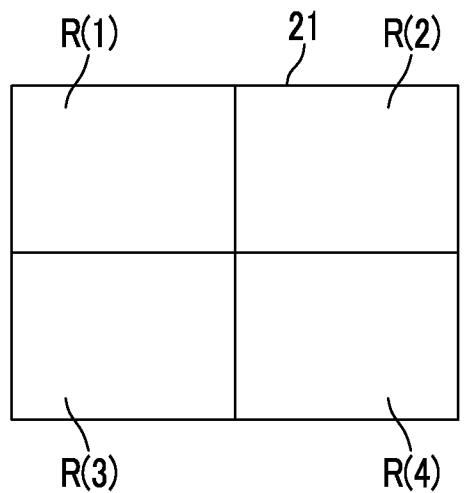
FIG. 4 is a diagram showing an example where an imaging area is divided into a plurality of partial imaging areas

At this time, how the imaging area is divided can be set automatically or manually. The imaging area can be divided into an arbitrary number of areas in the up-down direction and/or the right-left direction. For example, the imaging area may be divided into two areas right and left, and for example, as shown in FIG. 4, the imaging areas may be divided into four areas in total of two areas up and down and two areas right and left. FIG. 4 shows an example where an imaging area 21 is divided into four partial imaging areas R(1), R(2), R(3), and R(4) of two areas up and down and two areas right and left.

The lens unit 22 is attached to the imaging unit 20. The lens unit 22 includes, for example, a plurality of lenses, and the lenses are provided to be movable in an arrow Z direction in order to focus on the object S. The lens unit 22 also includes, for example, optical elements, such as a diaphragm and an excitation light cut filter, and adjusts the amount or wavelength of light to be detected.

The epi-illumination light source unit 24 and the transmission light source unit 26 respectively have, for example, an excitation light source for fluorescence imaging and a white light source, and is configured to switch between the light sources as necessary under the control of the imaging control device 100. For example, when performing imaging to detect fluorescence emitted from the fluorescence-labeled object S, the object S is irradiated with excitation light from the epi-illumination light source unit 24 or the transmission light source unit 26, when performing imaging to detect reflected light from the object S, the object S is irradiated with white light from the epi-illumination light source unit 24, and when performing imaging to detect transmitted light transmitted through the object S, the object S is irradiated with white light from the transmission light source unit 26.

The object observation monitor 50 displays a state on the stage 16 imaged with a small-sized camera (not shown) provided in the upper portion of the housing 12. With this, it is possible to confirm the position of the object S arranged on the stage 16 or the height of the stage 16, and to adjust the position of the object or the height of the stage such that the object S is arranged suitably for imaging.

The imaging control device 100 is constituted of, for example, a personal computer, and includes a control device body 102, an input unit 104, and a display unit 106. The imaging control device 100 controls the operation of the imaging unit 20, the epi-illumination light source unit 24, and the transmission light source unit 26 of the black box 10, and the black box 10 images the object S under the control of the imaging control device 100. In this embodiment, the imaging unit 20 in the black box 10 and the imaging control device 100 constitute an imaging device of the invention.

As shown in FIG. 3, the control device body 102 includes an image processing unit 108, a proper exposure time calculation unit 110, an imaging frequency setting unit 112, and a control unit 114. The control unit 114 includes, for example, a central processing unit (CPU), a read only memory (ROM), and the like. The control unit 114 integrally controls the respective units in the black box 10 and the operation of the imaging control device 100, and includes an imaging control unit 115 which controls the operation of the imaging unit 20, and a display control unit 116.

The proper exposure time calculation unit 110 calculates a proper exposure time T(i) based on an image signal acquired in the partial imaging area for each partial imaging area R(i) obtained by dividing the imaging area. Here, the proper exposure time T(i) means an exposure time of imaging until a signal value of the image signal in the partial imaging area R(i) reaches a target signal value set in advance. For example, the proper exposure time calculation unit 110 can perform pre-imaging using the imaging unit 20 before the start of imaging of main imaging, and can calculate the proper exposure time T(i) based on the image signal of each partial imaging area R(i) acquired through pre-imaging. Main imaging means imaging which is performed to obtain an image for analysis and spectrometry of the object, and pre-imaging means imaging which is preliminarily performed to obtain information for determining the exposure time of main imaging. In pre-imaging, a plurality of pixels may be recognized as one unit, and sensitivity of pre-imaging may be improved by a binning output or the like outputting image data of one unit as a pixel average. For example, when a plurality of samples as the object S are arranged at intervals on the stage 16, and imaging is performed while assigning a plurality of samples to a plurality of partial imaging areas, an exposure time suitable for a sample imaged in each partial imaging area R(i) is calculated as the proper exposure time T(i) by the proper exposure time calculation unit 110.

The imaging frequency setting unit 112 calculates a total imaging time Ttotal as a positive integer multiple of the maximum value Tmax among a plurality of proper exposure times T(i) calculated by the proper exposure time calculation unit 110, and sets an imaging frequency for each partial imaging area R(i) using a value obtained by dividing the total imaging time Ttotal by the proper exposure time T(i) of the partial imaging area R(i). Here, as a positive integer for use in calculating the total imaging time Ttotal, a minimum image addition frequency K set in advance automatically or manually can be used.

For example, the imaging frequency setting unit 112 sequentially divides the total imaging time Ttotal by the proper exposure time T(i) of each partial imaging area R(i), and when the total imaging time Ttotal is dividable by the proper exposure time T(i) of each partial imaging area R(i) (hereinafter, referred to as "case 1"), sets a value obtained by division as the imaging frequency of the partial imaging area. When the total imaging time Ttotal is not dividable by the proper exposure time T(i) of each partial imaging area R(i), and when an integer part of a value obtained by division is referred to as N(i), N(i) is set as the imaging frequency of the partial imaging area when the relationship with a threshold value Tth1 determined in advance is 0<Ttotal−(T(i)×N(i))<Tth1 (hereinafter, referred to as "case 2"), and a value obtained by adding 1 to N(i) can be set as the imaging frequency of the partial imaging area when Ttotal−(T(i)×N(i))≤Tth1 (hereinafter, referred to as "case 3").

The imaging control unit 115 performs control such that the imaging unit 20 successively and repeatedly performs imaging with the proper exposure time T(i) calculated by the proper exposure time calculation unit 110 in each partial imaging area R(i) by the imaging frequency set by the imaging frequency setting unit 112. Specifically, after imaging of main imaging in each partial imaging area R(i) starts, the imaging control unit 115 performs control such that the imaging unit 20 successively and repeatedly performs imaging with the proper exposure time T(i) the number of times corresponding to the value (the value obtained by dividing the total imaging time Ttotal by the proper exposure time T(i) of the partial imaging area R(i)) set as the imaging frequency in the partial imaging area R(i) of the "case 1", and successively and repeatedly performs imaging with the proper exposure time T(i) N(i) times in the partial imaging area R(i) of the "case 2". However, the imaging control unit 115 performs control such that the imaging unit 20 successively and repeatedly performs imaging with the proper exposure time T(i) to the N(i)-th time and then performs imaging of the (N(i)+1)th time with an exposure time of Ttotal−(T(i)×N(i)) exceptionally in the partial imaging area R(i) of the "case 3".

The image processing unit 108 generates an added image by simply adding or adding and averaging the image signal of each image successively imaged in each partial imaging area R(i) through main imaging. Simply adding of the image signal of each image successively imaged refers to that, for example, imaging is successively performed three times in total in a certain partial imaging area, and when the image signal of the first imaging is G1, the image signal of the second imaging is G2, and the image signal of the third imaging is G3, G1+G2+G3 is calculated as an added image. Addition averaging of the image signal of each image successively imaged refers to that (G1+G2+G3)/3 is calculated as an added image. At this time, the image processing unit 108 generates, as an added image, an image obtained by multiplying each pixel value of the image obtained by simply adding or adding and averaging the image signal of each image successively imaged by the value (coefficient) of Ttotal/(T(i)×N(i)) in the partial imaging area R(i) of the "case 2".

The display control unit 116 makes the display unit 106 display the added image of each partial imaging area R(i) generated by the image processing unit 108. The display unit 106 is constituted of, for example, a display device, such as a cathode ray tube (CRT) display or a liquid crystal display, and displays the added image of each partial imaging area R(i) generated by the image processing unit 108 as described above. The display unit 106 displays a setup screen for performing various settings or giving an instruction.

The input unit 104 includes a mouse, a keyboard, and the like. The user performs various settings or gives an instruction using the input unit 104. The user sets and inputs, for example, information regarding the division method of the imaging area, information regarding the minimum image addition frequency K, and the like using the input unit 104. The set and input information is stored in, for example, a storage unit (not shown) in the control unit 114.

The imaging system 1 has the above-described configuration, and can perform imaging using four imaging methods according to the type of object or the purpose of imaging. As the four imaging methods, there are an imaging method (hereinafter, referred to as a first imaging method) which detects chemiluminescence emitted from the object, an imaging method (hereinafter, referred to as a second imaging method) which detects fluorescence emitted from the object, an imaging method (hereinafter, referred to as a third imaging method) which detects reflected light reflected from the object, and an imaging method (hereinafter, referred to as a fourth imaging method) which detects transmitted light transmitted through the object.

In the first imaging method, when an object molecule excited by a chemical reaction is returned to a ground state, chemiluminescence in which energy is discharged as light is detected. In the first imaging method, light irradiation from the epi-illumination light source unit 24 and the transmission light source unit 26 is not performed. In the second imaging method, excitation light is irradiated from the epi-illumination light source unit 24 or the transmission light source unit 26, and fluorescence from a fluorescence substance labeling an imaging target substance in the object is detected. In the third imaging method, for example, white light is irradiated as illumination light from the epi-illumination light source unit 24, and reflected light of illumination light from the object is detected. In the fourth imaging method, for example, white light is irradiated as illumination light from the transmission light source unit 26, and transmitted light of illumination light transmitted through the object is detected.

Figure 5:
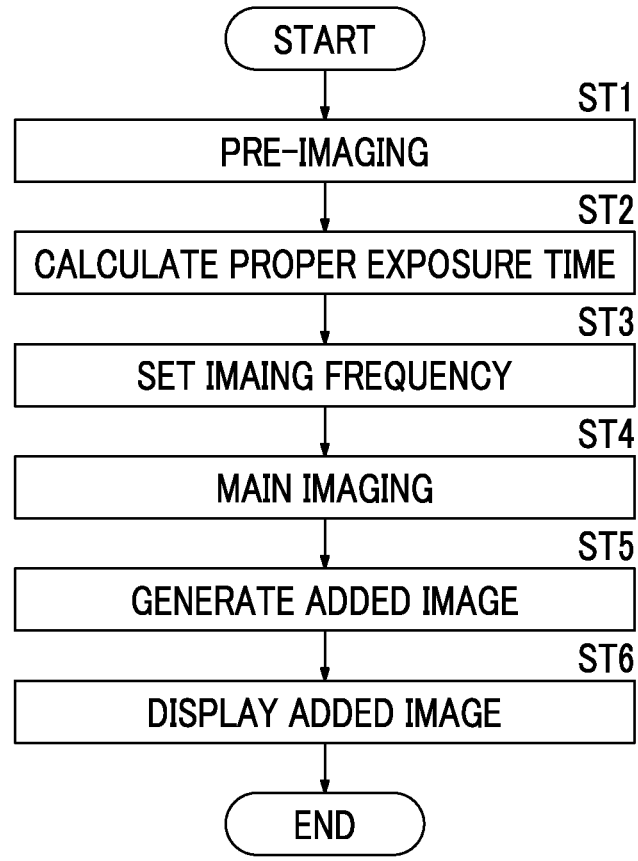
FIG. 5 is a flowchart showing the flow of a process which is performed by the imaging system of FIG. 1.

Next, the flow of a process which is performed by the imaging system 1 will be described referring to the flowchart shown in FIG. 5. Here, description will be provided assuming that the division method of the imaging area or the minimum image addition frequency K are set in advance, and the imaging area is divided into a plurality of partial imaging areas R(i) by the set division method. First, a plurality of samples as the object S are arranged at intervals on the stage 16 of the black box 10, and can be assigned to a plurality of partial imaging areas R(i) and imaged. Then, pre-imaging is performed using the imaging unit 20 (ST1). Next, the proper exposure time calculation unit 110 calculates the proper exposure time T(i) for each partial imaging area R(i) based on the image signal of each partial imaging area R(i) acquired through pre-imaging (ST2).

Next, the imaging frequency setting unit 112 calculates the total imaging time Ttotal by multiplying the maximum value Tmax among a plurality of proper exposure times T(i) calculated in Step ST2 by the minimum image addition frequency K, and sets the imaging frequency for each partial imaging area R(i) using a value obtained by dividing the total imaging time Ttotal by the proper exposure time T(i) of the partial imaging area R(i) (ST3). Specifically, the total imaging time Ttotal is divided by the proper exposure time T(i) of each partial imaging area R(i), and when the total imaging time Ttotal is dividable by the proper exposure time T(i) of each partial imaging area R(i) (case 1), a value obtained by division is set as the imaging frequency of the partial imaging area. When the total imaging time Ttotal is not dividable by the proper exposure time T(i) of each partial imaging area R(i), and when 0<Ttotal−(T(i)×N(i))<Tth1 (case 2), N(i) is set as the imaging frequency of the partial imaging area, and when Ttotal−(T(i)×N(i))≥Tth1 (case 3), a value obtained by adding 1 to N(i) is sets as the imaging frequency of the partial imaging area. Here, N(i) is an integer part of a value obtained by dividing the total imaging time Ttotal by the proper exposure time T(i) of each partial imaging area R(i), and Tth1 is a threshold value Tth1 determined in advance.

Next, main imaging is performed using the imaging unit 20 (ST4). In main imaging, the imaging control unit 115 performs control such that the imaging unit 20 successively and repeatedly performs imaging with the proper exposure time T(i) calculated in Step ST2 by the imaging frequency set in Step ST3 in each partial imaging area R(i). Specifically, the imaging control unit 115 performs control such that the imaging unit 20 starts imaging of main imaging in all partial imaging areas R(i) and successively and repeatedly performs imaging with the proper exposure time T(i) by the number of times corresponding to the value (the value obtained by dividing the total imaging time Ttotal by the proper exposure time T(i) of the partial imaging area R(i)) set as the imaging frequency in the partial imaging area R(i) of the "case 1", and the imaging unit 20 successively and repeatedly performs imaging with the proper exposure time T(i) by N(i) times in the partial imaging area R(i) of the "case 2". Furthermore, control is performed such that the imaging unit 20 successively and repeatedly performs imaging with the proper exposure time T(i) to the N(i)-th time and then performs imaging of the (N(i)+1)th time with an exposure time of Ttotal−(T(i)×N(i)) exceptionally in the partial imaging area R(i) of the "case 3".

Next, the image processing unit 108 simply adds or adds and averages the image signal of each image successively imaged in each partial imaging area R(i) through main imaging to generate an added image (ST5). At this time, the image processing unit 108 generates, as an added image, an image obtained by multiplying each pixel value of the image obtained by simply adding or adding and averaging the image signal of each image successively imaged by the value (coefficient) of Ttotal/(T(i)×N(i)) in the partial imaging area R(i) of the "case 2". Then, the display control unit 116 makes the display unit 106 display the added image of each partial imaging area R(i) generated in Step ST5 (ST6), and ends the process.

Hereinafter, a process which is performed by the imaging system 1 will be described using a specific example. For example, a case where as shown in FIG. 4, a division method which divides the imaging area 21 into four partial imaging areas R(1), R(2), R(3), and R(4) of two areas up and down and two areas right and left is set as the division method of the imaging area, the value of the minimum image addition frequency K is set to 2, and the value of the threshold value Tth1 is set to 2.5 is considered. Then, it is assumed that the proper exposure times of the partial imaging areas R(1), R(2), R(3), and R(4) calculated by the proper exposure time calculation unit 110 are respectively 3 seconds, 9 seconds, 4 seconds, and 6 seconds.

In this case, since the maximum value Tmax among a plurality of calculated proper exposure times is 9 seconds, the imaging frequency setting unit 112 first calculates 18 seconds obtained by multiplying 9 seconds by two (minimum image addition frequency multiple) as the total imaging time Ttotal. Then, in the partial imaging areas R(1), R(2), and R(4), since the total imaging time of 18 seconds is dividable by the proper exposure times of 3 seconds, 9 seconds, and 6 seconds of the partial imaging areas, as shown in Table 1 described below, values 6, 4, and 3 (times) obtained by division are set as the imaging frequency. Furthermore, in the partial imaging area R(3), since the total imaging time of 18 seconds is not dividable by the proper exposure time of 4 seconds of the partial imaging area, and this corresponds to a case of 0<Ttotal−(T(i)×N(i))<Tth1 (case 2), as shown in Table 1 described below, an integer part of 4 (times) of a value obtained by dividing the total imaging time of 18 seconds by the proper exposure time of 4 seconds is set as the imaging frequency.

TABLE 1

| Partial Imaging Area | Exposure Time | Imaging Frequency | Total Exposure Time | Coefficient |
|---|---|---|---|---|
| R(1) | 3 s | 6 | 18 s | 1 |
| R(2) | 9 s | 2 | 18 s | 1 |
| R(3) | 4 s | 4 | 16 s | 18/16 |
| R(4) | 6 s | 3 | 18 s | 1 |

Figure 6:
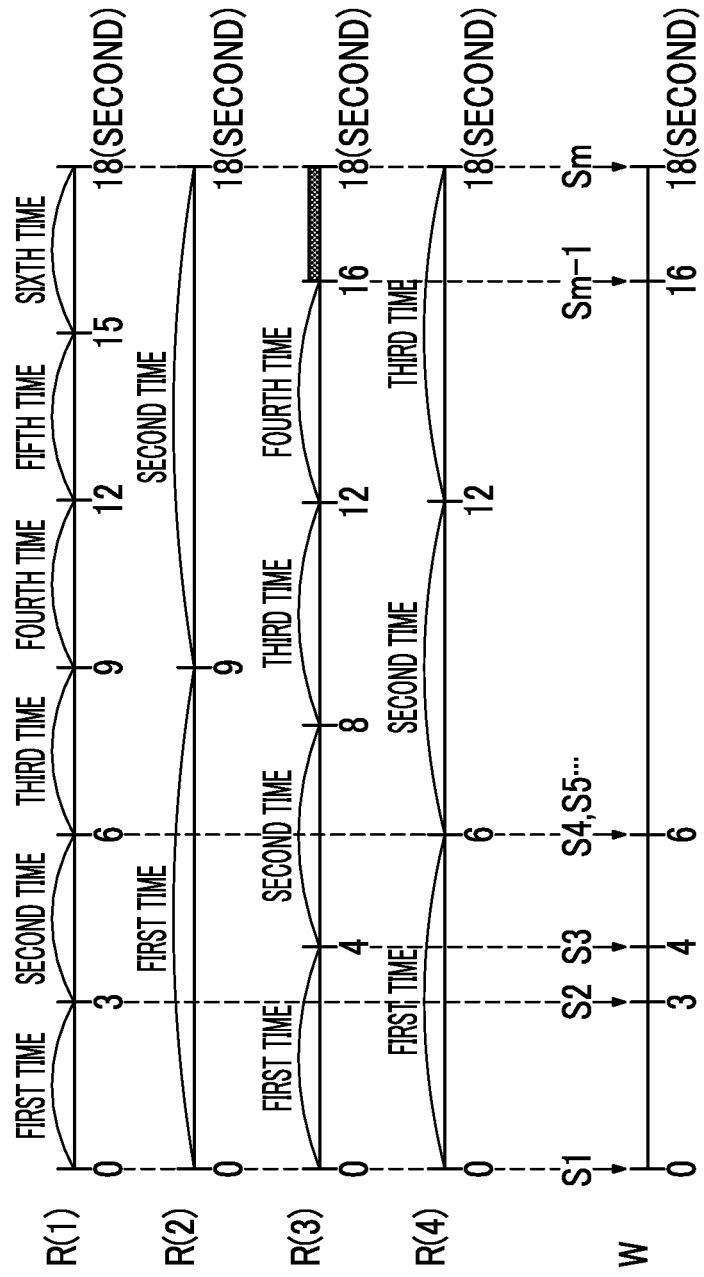
FIG. 6 is a time chart (first view) showing an example of imaging control in each partial imaging area.

Then, as shown in the time chart of FIG. 6, the imaging control unit 115 performs control such that the imaging unit 20 successively and repeatedly performs imaging with the proper exposure time T(i) in each partial imaging area R(i) by the set imaging frequency. FIG. 6 shows a time chart W of imaging control in the imaging control unit 115, in addition to the time chart of imaging in each partial imaging area R(i). As shown in the time chart W of FIG. 6, the imaging control unit 115 first starts imaging (exposure) of main imaging in all partial imaging areas R(1), R(2), R(3), and R(4) (S1), performs reading of the image signal of the first time and reset of the stored electric charge in the partial imaging area R(1) at the time point of 3 seconds from the start of imaging, and then starts the second imaging (storing of electric charge) (S2). Next, reading of the image signal of the first time and reset of the stored electric charge are performed in the partial imaging area R(3) at the time point of 4 seconds from the start of imaging, and then the second imaging (storage of electric charge) is started (S3).

Next, reading of the image signal of the second time and reset of the stored electric charge are performed in the partial imaging area R(1) at the time point of 6 seconds from the start of imaging, and then, the third imaging (storage of electric charge) is started (S4), and in the partial imaging area R(4), reading of the image signal of the first time and reset of the stored electric charge are performed, and then the second imaging (storage of electric charge) is started (S5). The same process continues to be performed, and reading of the image signal of the fourth time and reset of the stored electric charge are performed in the partial imaging area R(3) at the time point of 16 seconds from the start of imaging, and imaging ends in the partial imaging area R(3) (Sm-1). Then, reading of the final image signal and reset of the stored electric charge in each partial imaging area are performed for the partial imaging areas R(1), R(2), and R(4) at the time point of 18 seconds from the start of imaging, and then imaging end s (Sm).

With this, as shown in Table 1, while the total exposure time (exposure time×imaging frequency) in the partial imaging areas R(1), R(2), and R(4) is 18 seconds, the total exposure time in the partial imaging area R(3) is 16 seconds. Accordingly, the image processing unit 108 simply adds or adds and averages the image signal of each image successively imaged in each partial imaging area to generate an added image (the same as an image obtained through multiplication by a coefficient 1) for the partial imaging areas R(1), R(2), and R(4), and generates, as an added image, an image obtained by multiplying each pixel value of the image obtained by simply adding or adding and averaging the image signal of each image successively imaged by a coefficient 18/16 for the partial imaging area R(3).

In the description of the specific example (hereinafter, referred to as a "specific example 1") described above, although a case where the value of the threshold value Tth1 is 2.5 has been described, hereinafter, a case (hereinafter, referred to as a "specific example 2") where the conditions other than the threshold value Tth1 are the same and the value of the threshold value Tth is 1.5 which is only different from the specific example 1 will be described. In the specific example 2, as in the specific example 1, when the proper exposure times of the partial imaging areas R(1), R(2), R(3), and R(4) calculated by the proper exposure time calculation unit 110 are respectively 3 seconds, 9 seconds, 4 seconds, and 6 seconds, 18 seconds obtained by multiplying the proper exposure time of 9 seconds as the maximum value by two (minimum image addition frequency multiple) are calculated as the total imaging time Ttotal by the imaging frequency setting unit 112, and in the partial imaging areas R(1), R(2), and R(4), since the total imaging time of 18 seconds is dividable by the proper exposure times of 3 seconds, 9 seconds, and 6 seconds of the partial imaging areas, as shown in Table 2 described below, 6, 2, and 3 (times) obtained by division are set as the imaging frequency. In the partial imaging area R(3), unlike the specific example 1, the total imaging time of 18 seconds is not divided by the proper exposure time of 4 seconds of the partial imaging area, and this corresponds to a case of Ttotal−(T(i)×N(i)) Tth1 (case 3); thus, as shown in Table 2, a value (five times) obtained by adding 1 to an integer part of 4 obtained by dividing the total imaging time of 18 seconds by the proper exposure time of 4 seconds is set as the imaging frequency.

TABLE 2

| Partial Imaging Area | Exposure Time | Imaging Frequency | Total Exposure Time | Coefficient |
|---|---|---|---|---|
| R(1) | 3 s | 6 | 18 s | 1 |
| R(2) | 9 s | 2 | 18 s | 1 |
| R(3) | 4 s, 2 s | 5 | 18 s | 1 |
| R(4) | 6 s | 3 | 18 s | 1 |

Figure 7:
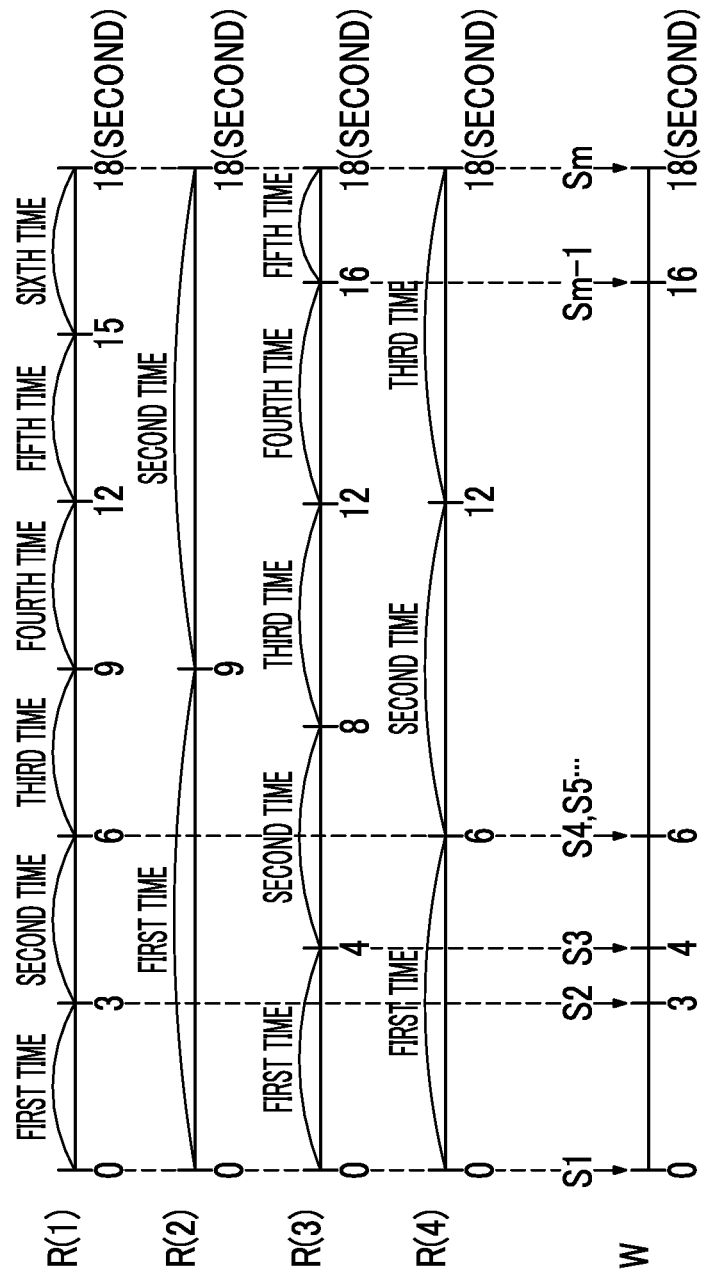
FIG. 7 is a time chart (second view) showing an example of imaging control in each partial imaging area.

In the specific example 2, as shown in the time chart of FIG. 7, the imaging control unit 115 performs control such that the imaging unit 20 successively and repeatedly performs imaging with the proper exposure time of 3 seconds, 9 seconds, and 6 seconds in the partial imaging areas R(1), R(2), and R(4) by the set imaging frequency, and the imaging unit 20 successively and repeatedly performs the first to fourth imaging with the proper exposure time of 4 seconds (T(3)) and then performs the fifth imaging (final imaging) with an exposure time of 2 seconds (=Ttotal−(T(3)×N(3)) in the partial imaging area R(3). That is, as shown in the time chart W of FIG. 7, the imaging control unit 115 performs the same control as in the specific example 1 until 16 seconds from the start of imaging after the start of imaging of main imaging, performs reading of the image signal of the fourth time and reset of the stored electric charge in the partial imaging area R(3) at the time point of 16 seconds from the start of imaging, and then starts the fifth imaging (storage of electric charge) (Sm-1). Then, reading of the final image signal and reset of the storage electric charge in each partial imaging area are performed for all partial imaging areas R(1), R(2), R(3), and R(4) at the time point of 18 seconds from the start of imaging, and then imaging ends (Sm).

Then, for each of the partial imaging areas R(1), R(2), R(3), and R(4), the image processing unit 108 simply adds or adds and averages the image signal of each image successively imaged in the partial imaging area to generate an added image (the same as an image obtained through multiplication by the coefficient of 1). In the specific example 2, as shown in Table 2, since the total exposure time (exposure time×imaging frequency) is 18 seconds which is the same in all partial imaging areas R(1), R(2), R(3), and R(4), the adjustment using a coefficient in the specific example 1 is not performed.

With the above configuration, according to the imaging system 1 of this embodiment, for performing imaging in the imaging unit 20 which is configured to divide the imaging area imaging the object into a plurality of partial imaging areas, to perform imaging for each partial imaging area, and to output the captured image, the proper exposure time calculation unit 110 calculates the proper exposure time based on the image signal acquired in the partial imaging area for each partial imaging area, the imaging frequency setting unit 112 sets the total imaging time as a positive integer multiple of the maximum value among a plurality of calculated proper exposure times, and sets the imaging frequency using the value obtained by dividing the total imaging time by the calculated proper exposure time of the partial imaging area for each partial imaging area, the imaging control unit 115 performs control such that the imaging unit 20 successively and repeatedly performs imaging with the calculated proper exposure time of the partial imaging area in each partial imaging area by the set imaging frequency of the partial imaging area, and the image processing unit 108 simply adds or adds and averages each image successively imaged in each partial imaging area. With this, for example, when a plurality of samples are collectively imaged, imaging is performed while assigning a plurality of samples to a plurality of partial imaging areas, and in each partial imaging area, it is possible to perform imaging with an exposure time suitable for a sample imaged in each partial imaging area, and to obtain an image with exposure suitable for each sample.

As described above, in the imaging system 1 of this embodiment, the imaging control unit 115 performs control such that the imaging unit 20 successively and repeatedly performs imaging with the calculated proper exposure time of the partial imaging area by the set imaging frequency of the partial imaging area in each partial imaging area, and the image processing unit 108 simply adds or adds and averages each image successively imaged in each partial imaging area; thus, it is possible to improve the signal-noise ratio (S/N) of the image imaged in each partial imaging area. Specifically, in the case of simple addition, since a signal component becomes n times, and a noise component becomes $\sqrt{n}$ times, the S/N is improved to $\sqrt{n}$ times. In the case of addition averaging, since a signal component becomes one time, and a noise component becomes $1/\sqrt{n}$ times, the S/N is improved to $\sqrt{n}$ times.

In the foregoing embodiment, although a case where the proper exposure time T(i) of each partial imaging area R(i) is calculated based on the image signal of each partial imaging area R(i) acquired through pre-imaging has been described, a CMOS image sensor may be used as an imaging element, and the proper exposure time T(i) of each partial imaging area R(i) may be calculated based on the image signal of each partial imaging area R(i) nondestructively read from the imaging element after the start of imaging. Nondestructive reading refers to a method which, for reading an image signal from the imaging element, reads the image signal while maintaining the storage state without emptying electric charge stored in each photoelectric conversion element constituting the imaging element. That is, since a reset process is not performed for reading the image signal, it is possible to read the image signal any number of times in the middle of storing electric charge.

In the foregoing embodiment, although a case where the imaging frequency setting unit 112 sets the imaging frequency while classifying a case where the total imaging time Ttotal is not dividable by the proper exposure time T(i) of the partial imaging area R(i) into the "case 2" and the "case 3" according to the relationship with the threshold value Tth1 determined in advance has been described, alternatively, the imaging frequency setting unit 112 may set the imaging frequency while performing classification according to the relationship with a different threshold value Tth2 determined in advance. Specifically, when the total imaging time Ttotal is not dividable by the proper exposure time T(i) of the partial imaging area R(i), a value obtained by adding 1 to N(i) can be set as the imaging frequency of the partial imaging area when (T(i)×(N(i)+1))−Ttotal≤Tth2 (hereinafter, referred to as "case 4"), and N(i) can be set as the imaging frequency of the partial imaging area when (T(i)×(N(i)+1))−Ttotal>Tth2 (hereinafter, referred to as "case 5").

At this time, for the partial imaging area R(i) of the "case 4", the image processing unit 108 can generate, as an added image, an image obtained by multiplying each pixel of the image obtained by simply adding or adding and averaging the image signal of each image successively imaged by the value (coefficient) of Ttotal/(T(i)×(N(i)+1)). For the partial imaging area R(i) of the "case 5", an image obtained by multiplying each pixel value of the image obtained by simply adding or adding and averaging the image signal of each image successively imaged by the value (coefficient) of Ttotal/(T(i)×N(i)) can be generated as an added image.

Hereinafter, a process for setting an imaging frequency according to the relationship with the threshold value Tth2 and generating an added image will be described using a specific example. For example, a case (hereinafter, referred to as a "specific example 3") where the conditions other than the threshold value Tth2 are the same and the value of the threshold Tth2 is set to 2.5 which is only different from the specific example 1 is considered. In the specific example 3, as in the specific example 1, when the proper exposure times of the partial imaging areas R(1), R(2), R(3), and R(4) calculated by the proper exposure time calculation unit 110 are respectively 3 seconds, 9 seconds, 4 seconds, and 6 seconds, 18 seconds obtained by multiplying the proper exposure time of 9 seconds as the maximum value by two (minimum image addition frequency multiple) are calculated as the total imaging time Ttotal by the imaging frequency setting unit 112, and in the partial imaging areas R(1), R(2), and R(4), since the total imaging time of 18 seconds is dividable by the proper exposure times of 3 seconds, 9 seconds, and 6 seconds of the partial imaging areas, as shown in Table 3 described below, values 6, 2, and 3 (times) obtained by division are set as an imaging frequency. In the partial imaging area R(3), unlike the specific example 1, since the total imaging time of 18 seconds is not dividable by the proper exposure time of 4 seconds of the partial imaging area, and this corresponds to a case of (T(i)×(N(i)+1))−Ttotal≤Tth2 (case 4), as shown in Table 3 described below, a value (five times) obtained by adding 1 to an integer part of 4 of a value obtained by dividing the total imaging time of 18 seconds by the proper exposure time of 4 seconds is set as the imaging frequency.

TABLE 3

| Partial Imaging Area | Exposure Time | Imaging Frequency | Total Exposure Time | Coefficient |
|---|---|---|---|---|
| R(1) | 3 s | 6 | 18 s | 1 |
| R(2) | 9 s | 2 | 18 s | 1 |
| R(3) | 4 s | 5 | 20 s | 18/20 |
| R(4) | 6 s | 3 | 18 s | 1 |

Figure 8:
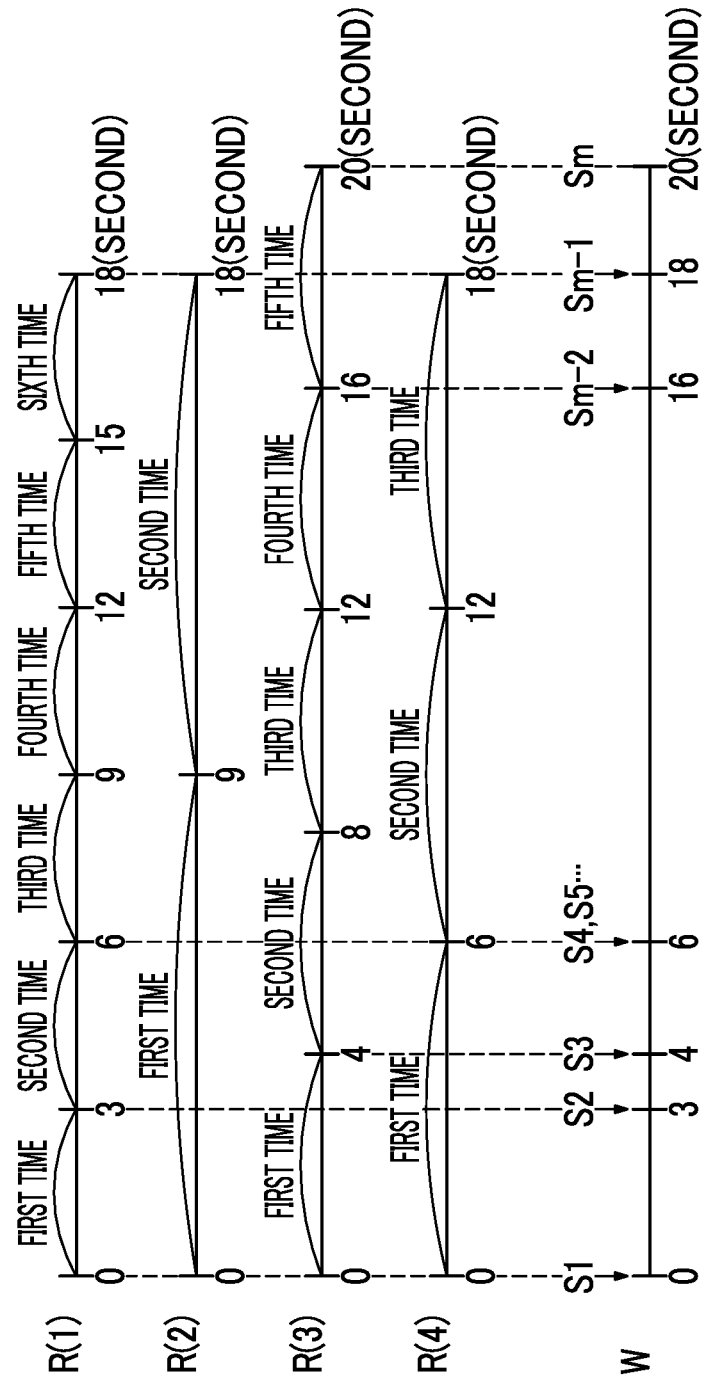
FIG. 8 is a time chart (third view) showing an example of imaging control in each partial imaging area.

As shown in the time chart of FIG. 8, the imaging control unit 115 performs control such that the imaging unit 20 successively and repeatedly performs imaging with the proper exposure time T(i) by the set imaging frequency in each partial imaging area R(i). That is, as shown in the time chart W of FIG. 8, the imaging control unit 115 performs the same control as in the specific example 1 until 16 seconds from the start of imaging after the start of imaging of main imaging, performs reading of the image signal of the fourth time and reset of the stored electric charge in the partial imaging area R(3) at the time point of 16 seconds from the start of imaging, and then starts the fifth imaging (storage of electric charge) (Sm-2). Then, reading of the final image signal and reset of the stored electric charge in each partial imaging area are performed in the partial imaging areas R(1), R(2), and R(4) at the time point of 18 seconds from the start of imaging, and then imaging ends (Sm-1). Then, reading of the final image signal and reset of the stored electric charge are performed in the partial imaging area R(3) at the time point of 20 seconds from the start of imaging, and then imaging ends (Sm).

With this, as shown in Table 3, while the total exposure time (exposure time×imaging frequency) in the partial imaging areas R(1), R(2), and R(4) is 18 seconds, the total exposure time in the partial imaging area R(3) is 20 seconds. Accordingly, the image processing unit 108 simply adds or adds and averages the image signal of each image successively imaged in each partial imaging area to generate an added image (the same as an image obtained through multiplication by a coefficient 1) for the partial imaging areas R(1), R(2), and R(4), and generates, as an added image, an image obtained by multiplying each pixel value of the image obtained by simply adding or adding and averaging the image signal of each image successively imaged by a coefficient 18/20 for the partial imaging area R(3).

What is claimed is:

1. An imaging device comprising:
    an image sensor which is configured to divide an imaging area imaging an object into a plurality of partial imaging areas, to perform imaging for each partial imaging area, and to output the captured image; and a processor configured to
        calculate a proper exposure time for each partial imaging area based on an image signal acquired in each partial imaging area;
        set a total imaging time as a positive integer multiple of a maximum value among the plurality of the proper exposure times for each partial imaging area calculated by the processor, and set an imaging frequency for each partial imaging area using a value obtained by dividing the total imaging time by the proper exposure time for each partial imaging area calculated by the processor:
        perform control such that, in each partial imaging area, the image sensor successively and repeatedly performs imaging with the proper exposure time for each partial imaging area calculated by the processor and by the imaging frequency set for each partial imaging area; and
        simply add or add and average the image signal of each image successively imaged in each partial imaging area.

2. The imaging device according to claim 1,
wherein the imaging area is constituted of an imaging element from which an image signal of the imaging area is readable nondestructively.

3. The imaging device according to claim 1, further comprising: an input unit which receives an input from the user,
wherein, when the input for designating how the imaging area is divided is received by the input unit from the user, the image sensor divides the imaging area into the plurality of partial imaging areas according to the designation.

4. The imaging device according to claim 2, further comprising: an input unit which receives an input from the user,
wherein, when the input for designating how the imaging area is divided is received by the input unit from the user, the image sensor divides the imaging area into the plurality of partial imaging areas according to the designation.

5. The imaging device according to claim 1,
wherein the image sensor performs pre-imaging in the imaging area, and the processor calculates the proper exposure time based on the signal of each partial imaging area acquired through the pre-imaging performed in the imaging area.

6. The imaging device according to claim 2,
wherein the image sensor performs pre-imaging in the imaging area, and the processor calculates the proper exposure time based on the image signal of each partial imaging area acquired through the pre-imaging performed in the imaging area.

7. The imaging device according to claim 3, wherein the image sensor performs pre-imaging in the imaging area, and the processor calculates the proper exposure time based on the image signal of each partial imaging area acquired through the pre-imaging performed in the imaging area.

8. The imaging device according to claim 1, wherein, when the total imaging time is Ttotal, a natural number equal to or less than the number of partial imaging areas is i, the proper exposure time of an i-th partial imaging area among the plurality of partial imaging areas is T(i), an integer part of a value obtained by dividing the total imaging time by the proper exposure time of the i-th partial imaging area is N(i), and a threshold value determined in advance is Tth1, for the partial imaging area where Ttotal−(T(i)×N(i))>Tth1, the processor sets a value obtained by adding 1 to N(i) as the imaging frequency of the partial imaging area.

9. The imaging device according to claim 2, wherein, when the total imaging time is Ttotal, a natural number equal to or less than the number of partial imaging areas is i, the proper exposure time of an i-th partial imaging area among the plurality of partial imaging areas is T(i), an integer part of a value obtained by dividing the total imaging time by the proper exposure time of the i-th partial imaging area is N(i), and a threshold value determined in advance is Tth1, for the partial imaging area where Ttotal−(T(i)×N(i))>Tth1, the processor sets a value obtained by adding 1 to N(i) as the imaging frequency of the partial imaging area.

10. The imaging device according to claim 3, wherein, when the total imaging time is Ttotal, a natural number equal to or less than the number of partial imaging areas is i, the proper exposure time of an i-th partial imaging area among the plurality of partial imaging areas is T(i), an integer part of a value obtained by dividing the total imaging time by the proper exposure time of the i-th partial imaging area is N(i), and a threshold value determined in advance is Tth1, for the partial imaging area where Ttotal−(T(i)×N(i))>Tth1, the processor sets a value obtained by adding 1 to N(i) as the imaging frequency of the partial imaging area.

11. The imaging device according to claim 4, wherein, when the total imaging time is Ttotal, a natural number equal to or less than the number of partial imaging areas is i, the proper exposure time of an i-th partial imaging area among the plurality of partial imaging areas is T(i), an integer part of a value obtained by dividing the total imaging time by the proper exposure time of the i-th partial imaging area is N(i), and a threshold value determined in advance is Tth1, for the partial imaging area where Ttotal−(T(i)×N(i))>Tth1, the processor sets a value obtained by adding 1 to N(i) as the imaging frequency of the partial imaging area.

12. The imaging device according to claim 8, Wherein the processor performs control such that the image sensor successively and repeatedly performs imaging with the proper exposure time of the partial imaging area to the N(i)-th time and then performs the (N(i)+I)th imaging with an exposure time of Ttotal−(T(i)×N(i)) exceptionally in the partial imaging area where Ttotal−(T(i)×N(i))>Tth1.

13. The imaging device according to claim 8, wherein the processor sets N(i) as the imaging frequency of the partial imaging area for the partial imaging area where 0<Ttotal−(T(i)×N(i))<Tth1, and the processor multiplies each pixel value of an image obtained by simply adding or adding and averaging the image signal of each image successively imaged in the partial imaging area by a value of Ttotal/(T(i)×N(i)) for the partial imaging area where 0<Ttotal−(T(i)×N(i))<Tth1.

14. The imaging device according to claim 12, wherein the processor sets N(i) as the imaging frequency of the partial imaging area for the partial imaging area where 0<Ttotal−(T(i)×N(i))<Tth1, and the processor multiplies each pixel value of an image of the object captured by the imaging device by simply adding or adding and averaging the image signal of each image successively imaged in the partial imaging area by a value of Ttotal/(T(i)×N(i)) for the partial imaging area where 0<Ttotal−(T(i)×N(i))<Tth1.

15. The imaging device according to claim 1, wherein, when the total imaging time is Ttotal, a natural number equal to or less than the number of partial imaging areas is i, the proper exposure time of an i-th partial imaging area among the plurality of partial imaging areas is T(i), an integer part of a value obtained by dividing the total imaging time by the proper exposure time of the i-th partial imaging area is N(i), and a threshold value determined in advance is Tth2, the processor sets a value obtained by adding 1 to N(i) as the imaging frequency of the partial imaging area for the partial imaging area where (T(i)×(N(i)+1))−Ttotal<Tth2.

16. The imaging device according to claim 2, wherein, when the total imaging time is Ttotal, a natural number equal to or less than the number of partial imaging areas is i, the proper exposure time of an i-th partial imaging area among the plurality of partial imaging areas is T(i), an integer part of a value obtained by dividing the total imaging time by the proper exposure time of the i-th partial imaging area is N(i), and a threshold value determined in advance is Tth2, the processor sets a value obtained by adding 1 to N(i) as the imaging frequency of the partial imaging area for the partial imaging area where (T(i)×(N(i)+1))−Ttotal<Tth2.

17. The imaging device according to claim 3, wherein, when the total imaging time is Ttotal, a natural number equal to or less than the number of partial imaging areas is i, the proper exposure time of an i-th partial imaging area among the plurality of partial imaging areas is T(i), an integer part of a value obtained by dividing the total imaging time by the proper exposure time of the i-th partial imaging area is N(i), and a threshold value determined in advance is Tth2, the processor sets a value obtained by adding 1 to N(i) as the imaging frequency of the partial imaging area for the partial imaging area where (T(i)×(N(i)+1))−Ttotal<Tth2.

18. The imaging device according to claim 5, wherein, when the total imaging time is Ttotal, a natural number equal to or less than the number of partial imaging areas is i, the proper exposure time of an i-th partial imaging area among the plurality of partial imaging areas is T(i), an integer part of a value obtained by dividing the total imaging time by the proper exposure time of the i-th partial imaging area is N(i), and a threshold value determined in advance is Tth2, the processor sets a value obtained by adding 1 to N(i) as the imaging frequency of the partial imaging area for the partial imaging area where (T(i)×(N(i)+1))−Ttotal<Tth2.

19. The imaging device according to claim 15, wherein the processor multiplies each pixel value of an image of the object captured by the imaging device by simply adding or adding and averaging the image signal of each image successively imaged in the partial imaging area by a value of Ttotal/(T(i)×(N(i)+1)) for the partial imaging area where (T(i)×(N(i)+1))−Ttotal<Tth2.

20. An imaging method which performs imaging using an imaging device having an image sensor and a processor, wherein the image sensor is configured to divide an imaging area imaging an object into a plurality of partial imaging areas, to perform imaging for each partial imaging area, and to output the captured image, the imaging method comprising:

calculating, by the processor, a proper exposure time for each partial imaging area based on an image signal acquired in each partial imaging area;

setting a total imaging time as a positive integer multiple of a maximum value among the plurality of the proper exposure times for each partial imaging area calculated by the processor, and setting an imaging frequency for each partial imaging area using a value obtained by dividing the total imaging time by the proper exposure time for each partial imaging area calculated by the processor:

successively and repeatedly performing imaging with the proper exposure time for each partial imaging area calculated by the processor and by the imaging frequency set for each partial imaging area and simply adding or adding and averaging the image signal of each image successively imaged in each partial imaging area.

* * * * *